(12) United States Patent
Satake

(10) Patent No.: US 8,668,335 B2
(45) Date of Patent: Mar. 11, 2014

(54) OPHTHALMIC PHOTOGRAPHING APPARATUS

(75) Inventor: Norimasa Satake, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/363,473

(22) Filed: Feb. 1, 2012

(65) Prior Publication Data

US 2012/0200824 A1   Aug. 9, 2012

(30) Foreign Application Priority Data

Feb. 4, 2011   (JP) .................................. 2011-023185

(51) Int. Cl.
*A61B 3/14*   (2006.01)

(52) U.S. Cl.
USPC .......................................... 351/206; 351/205

(58) Field of Classification Search
USPC .................. 351/206, 200, 209, 210
See application file for complete search history.

(56) References Cited

U.S. PATENT DOCUMENTS

| | | | |
|---|---|---|---|
| 5,463,430 A | 10/1995 | Isogai et al. | |
| 5,847,805 A * | 12/1998 | Kohayakawa et al. | 351/210 |
| 6,079,828 A * | 6/2000 | Fujieda | 351/206 |
| 6,810,140 B2 * | 10/2004 | Yang et al. | 382/154 |
| 7,222,963 B2 * | 5/2007 | Suzuki | 351/209 |
| 2005/0174536 A1 * | 8/2005 | Hanaki et al. | 351/205 |
| 2008/0024721 A1 | 1/2008 | Ueno et al. | |
| 2011/0102742 A1 * | 5/2011 | Miyasa et al. | 351/206 |

FOREIGN PATENT DOCUMENTS

JP   6046999 A   2/1994
JP   2008029467 A   2/2008

* cited by examiner

*Primary Examiner* — Evelyn A. Lester
*Assistant Examiner* — William Alexander
(74) *Attorney, Agent, or Firm* — Rankin, Hill & Clark LLP

(57) ABSTRACT

An ophthalmic photographing apparatus includes: an interference optical system having a light source, a splitter for splitting light from the light source into measurement light traveling toward an examinee's eye and reference light, and an optical detector for receiving combined light of the measurement light reflected by the examinee's eye and the reference light; an optical scanner arranged in an optical path of the measurement light to scan a photographing region of the examinee's eye with the measurement light; a controller for obtaining a tomographic image of the photographing region by controlling the optical scanner and processing an output signal from the optical detector; and an image processor for obtaining a combined tomographic image by combining a plurality of tomographic images corresponding to a plurality of different incident angles.

10 Claims, 8 Drawing Sheets

OPHTHALMIC PHOTOGRAPHING APPARATUS

CROSS-REFERENCE TO RELATED APPLICATION

This application claims priority from Japanese Patent Application No. 2011-023185 filed with the Japan Patent Office on Feb. 4, 2011, the entire content of which is hereby incorporated by reference.

BACKGROUND

1. Technical Field

The embodiments disclosed herein relate to an ophthalmic photographing apparatus for observing a tomographic image of a fundus of an examinee's eye.

2. Related Art

An optical coherence tomography (OCT) allows a tomographic image of an examinee's eye (e.g., a fundal tomographic image) to be obtained by scanning the fundus with measurement light using an optical scanning part. The tomographic image obtained by the OCT is then used for evaluating the state of the eye (See, for example, JP-A-2008-29467)

SUMMARY

An ophthalmic photographing apparatus comprises: an interference optical system having a light source, a splitter configured to split light emitted from the light source into measurement light traveling toward an examinee's eye and reference light, and an optical detector configured to receive combined light of the measurement light reflected by the examinee's eye and the reference light; an optical scanner configured to be arranged in an optical path of the measurement light and to scan a photographing region of the examinee's eye with the measurement light; a controller configured to obtain a tomographic image of the photographing region by controlling the optical scanner and processing an output signal from the optical detector; and an image processor configured to obtain a combined tomographic image by combining a plurality of tomographic images corresponding to a plurality of different incident angles.

DESCRIPTION OF EMBODIMENTS

Figure 1:
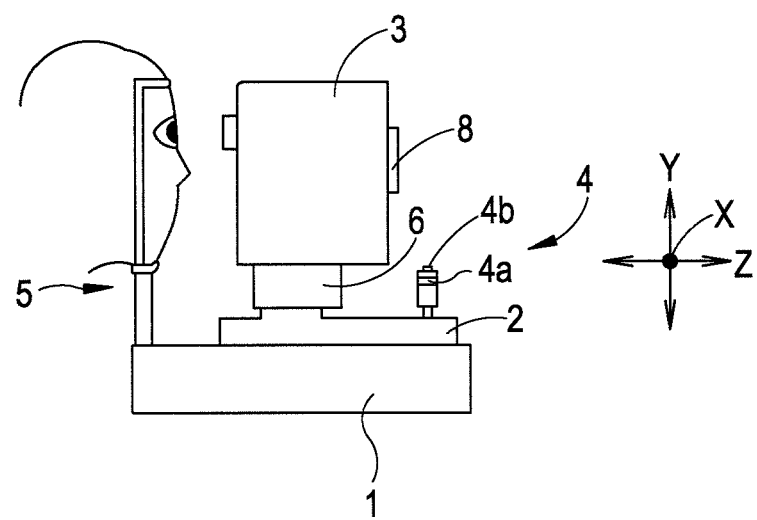
FIG. 1 is a diagram illustrating an external configuration of an ophthalmic photographing apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

When a tomographic image of an examinee's eye is obtained, there are cases where imaging of the eye is difficult. For example, a backside of a retinal blood vessel is not captured as an image since measurement light is blocked by the vessel. Consequently, a missing portion is generated in an image. Moreover, there are cases where reflection intensity varies depending on an incident angle of measurement light due to a retinal tissue structure (e.g., a scanning direction of a fibrous structure in a fundus layer). Such a case may cause a portion that is difficult to be imaged.

A technical aspect of embodiments is to provide an ophthalmic photographing apparatus capable of obtaining a good tomographic image suitable for measurement or observation.

The ophthalmic photographing apparatus according to an embodiment can have a configuration as follows.

(1) An ophthalmic photographing apparatus comprises: an interference optical system having a light source, a splitter configured to split light emitted from the light source into measurement light traveling toward an examinee's eye and reference light, and an optical detector configured to receive combined light of the measurement light reflected by the examinee's eye and the reference light: an optical scanner configured to be arranged in an optical path of the measurement light and to scan a photographing region of the examinee's eye with the measurement light; a controller configured to obtain a tomographic image of the photographing region by controlling the optical scanner and processing an output signal from the optical detector; and an image processor configured to obtain a combined tomographic image by combining a plurality of tomographic images corresponding to a plurality of different incident angles.

(2) In the ophthalmic photographing apparatus according to (1), the image processor corrects a difference in inclination of photograph portions among the plurality of tomographic images corresponding to the plurality of different incident angles.

(3) The ophthalmic photographing apparatus according to (1) further comprises: an incident angle changing unit configured to change an incident angle of the measurement light with respect to the photographing region.

(4) In the ophthalmic photographing apparatus according to (3), a fundus of the examinee's eye is photographed, and the incident angle changing unit changes the incident angle of the measurement light with respect to the fundus by changing an incident position of the measurement light with respect to a cornea of the eye.

(5) In the ophthalmic photographing apparatus according to (3), the incident angle changing unit includes a guide unit configured to set the incident angle of the measurement light to a predetermined angle.

(6) In the ophthalmic photographing apparatus according to (1), the plurality of tomographic images corresponding to the plurality of different incident angles are images relating to substantially the same photographing region.

(7) The ophthalmic photographing apparatus according to (3) further comprises: an apparatus main body configured to house the interference optical system and the optical scanner, wherein the incident angle changing unit is a drive part configured to move the apparatus main body.

(8) In the ophthalmic photographing apparatus according to (3), the incident angle changing unit is an optical member configured to change the incident angle of the measurement light.

According to the ophthalmic photographing apparatus of the embodiment, a missing image portion in a tomographic image or a portion that is difficult to be captured as an image due to a retinal tissue structure can be imaged.

Now, an ophthalmic photographing apparatus (the present apparatus) according to the present embodiment is described with reference to the accompanying drawings. FIG. 1 is a diagram illustrating an external configuration of the present apparatus.

The present apparatus includes a base 1, a movable base 2, a photographing part (apparatus main body) 3, and a face supporting unit 5. The movable base 2 is movable in a right-left direction (X direction) and a front-rear (working distance) direction (Z direction) relative to the base 1. The photographing part 3 is arranged on the movable base 2 so as to be movable in a three dimensional direction. The photographing part 3 houses therein an optical system, which is described later. The face supporting unit 5 is fixedly arranged to the base 1 to support a face of an examinee. The present apparatus includes an automatic moving mechanism. The automatic moving mechanism includes an electric motor for allowing a relative displacement of the photographing part 3 with respect to an examinee's eye. Specifically, an XYZ drive part 6 allows the photographing part 3 to move in a right-left direction, a vertical direction (Y direction), and a front-rear direction relative to an examinee's eye E. The XYZ drive part 6 serves as an electric drive part, and is arranged on the movable base 2.

The present apparatus also includes a manual moving mechanism having an operation member (joystick 4). The photographing part 3 is moved relative to the examinee's eye with operation of the operation member. Specifically, the present apparatus includes a sliding mechanism (not shown) that allows the movable base 2 to slide in XZ directions on the base 1. When the joystick 4 is operated, the movable base 2 is slid in XZ directions on the base 1. When a rotation knob 4a is rotationally operated, the XYZ drive part 6 moves the photographing part 3 in the Y direction. The photographing part 3 has a monitor 8 arranged on an examiner side thereof. The monitor 8 displays a fundus observation image, a fundus photographic image, a fundus tomographic image, an anterior segment observation image, and the like.

Figure 2:
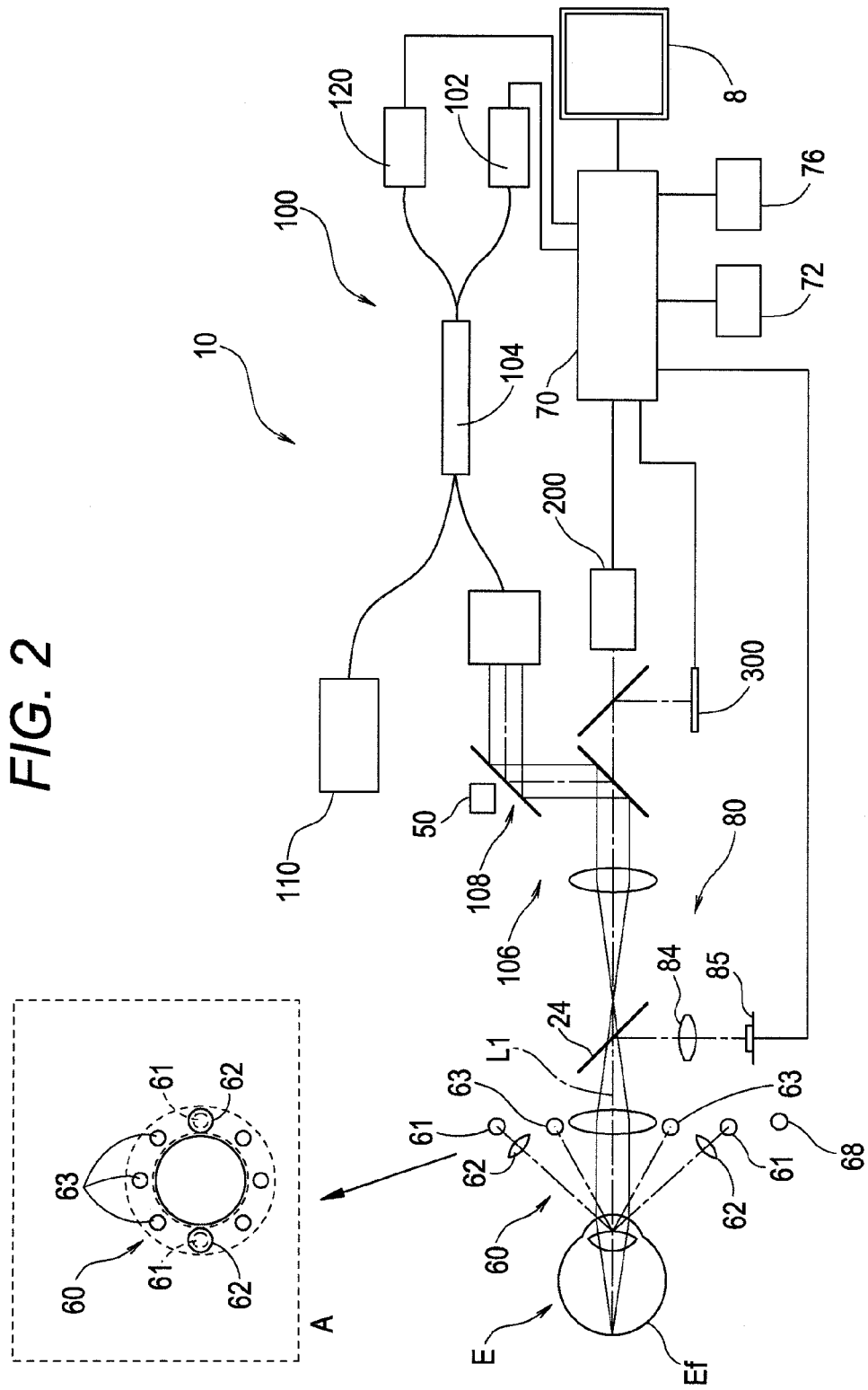
FIG. 2 is a schematic diagram illustrating the configurations of optical and control systems housed in a photographing part.

FIG. 2 is a schematic diagram illustrating a configuration of an optical system and a control system stored (installed) in the photographing part 3. In the present embodiment, assume that an axial direction, a horizontal direction, and a vertical direction of an examinee's eye (eye E) are Z direction, X direction, and Y direction, respectively. A surface direction of a fundus may be considered as XY directions.

A schematic configuration of the present apparatus is now described. The present apparatus serves as an optical coherence tomography (OCT) device 10 for photographing a tomographic image of a fundus Ef of the examinee's eye E. The OCT device 10 includes an alignment target projecting optical system 60, an anterior segment observation optical system 80, an interference optical system (OCT optical system) 100, a front observation optical system 200, a fixation target projecting unit 300, and a computation control part (e.g., CPU) 70.

The OCT optical system 100 irradiates a fundus with measurement light. The OCT optical system 100 detects an interference state between the measurement light reflected by the fundus and reference light by using a light receiving device (detector) 120. The OCT optical system 100 includes an irradiation position changing unit (e.g., an optical scanner 108 and the fixation target projecting unit 300) for changing an irradiation position of measurement light on the fundus Ef so that a photographing position on the fundus Ef is changed. The control part 70 controls operation of the irradiation position changing unit based on photographing position information which is set. The control part 70 obtains a tomographic image based on a light receiving signal from the detector 120.

<OCT Optical System>

The OCT optical system 100 has a configuration of an ophthalmic interferometer of optical coherence tomography (OCT), and photographs a tomographic image of an eye of a patient. The OCT optical system 100 divides the light emitted from measurement light source 102 into measurement light (a sample light) and reference light by using a coupler (optical divider) 104. The OCT optical system 100 guides the measurement light to the fundus Ef of the eye E by using a measurement optical system 106. The OCT optical system 100 guides the reference light to a reference optical system 110. Then, the detector (light receiving device) 120 detects an interfering light obtained by combining the measurement light reflected by the fundus Ef and the reference light.

The detector 120 detects an interference state between measurement light and reference light. In Fourier domain OCT, the detector 120 detects spectrum intensity of an interfering light. Therefore, spectrum intensity data can be Fourier transformed to obtain a depth profile (an A-scan signal) in a predetermined range. Examples of the Fourier domain OCT include a spectral-domain OCT (SD-OCT), swept-source OCT (SS-OCT), and a time-domain OCT (TD-OCT).

In the SD-OCT, a low coherent light source (a wide range light source) is used as the light source 102. The detector 120 includes a spectral optical system (spectrometer) for dispersing interference light into frequency components (wavelength components). The spectrometer, for example, includes a diffraction grating and a line sensor.

In the SS-COT, a wavelength scanning light source (wavelength changeable light source) is used as the light source 102. The wavelength scanning light source can change an outgoing wavelength at high speed in time. Moreover, for example, a single light receiving device is arranged as the detector 120. The light source 102, for example, includes a light source, a fiber ring resonator, and a wavelength selection filter. The wavelength selection filter is, for example, a combination of a diffraction grating and a polygon mirror, and a Fabry-Perot Etalon filter.

The light emitted from the light source 102 is split into measurement light flux and reference light flux by the coupler 104. The measurement light flux passes through an optical fiber and is the emitted to the air. The measurement light flux is then condensed on the fundus Ef through the optical scanner 108 and other optical members of the measurement optical system 106. Then, the light reflected by the fundus Ef travels back to the optical fiber through substantially the same optical path.

The optical scanner 108 scans the fundus with measurement light in XY directions (a transverse direction). The optical scanner 108 is arranged in a position substantially conjugated with a pupil. The optical scanner 108 includes two galvanometer mirrors, for example. A reflection angle of each of the galvanometer mirrors is optionally adjusted by a drive mechanism 50.

Consequently, a reflection (traveling) direction of the light flux emitted from the light source 102 can be changed. Thus, the fundus can be scanned with the measurement light in an optional direction. Therefore, a photographing position on the fundus Ef can be changed. The optical scanner 108 may be configured to deflect light. For example, a reflection mirror (a galvanometer mirror, a polygon mirror, a resonant scanner) or an acousto-optic modulator (AOM) for changing a traveling (deflection) direction of light can be used as the optical scanner 108.

The reference optical system 110 generates reference light to be combined with a reflection light obtained by reflection of measurement light by the fundus Ef. The reference optical system 110 may be Michelson type or Mach-Zehnder type. The reference optical system 110, for example, includes a reflecting optical system (e.g., a reference mirror). The reference optical system 110 reflects the light from the coupler 104 by using the reflecting optical system. Thus, the light is returned to the coupler 104 and is guided to the detector 120. Alternatively, the reference optical system 110 may include a transmitting optical system (e.g., an optical fiber). In such a case, the reference optical system 110 guides the light from the coupler 104 to the detector 120 by transmitting therethrough without the return of the light to the coupler 104.

The reference optical system 110 includes a member for changing a difference in length of optical paths for measurement light and reference light by moving an optical member in the reference optical path. In the reference optical system 110, for example, a reference mirror is moved in an optical axis direction. The member for changing the optical path length difference may be arranged in the measurement optical path of the measurement optical system 106.

<Front Observation Optical System>

The front observation optical system 200 is placed to obtain a front image of the fundus Ef. The front observation optical system 200 is configured as, for example, a scanning laser ophthalmoscope (SLO). The observation optical system 200 includes, for example, an optical scanner and a second light receiving device. The optical scanner two-dimensionally scans a fundus with measurement light (e.g., an infrared light) emitted from a light source. The second light receiving device receives a fundus reflection light through a confocal aperture arranged in a position substantially conjugated with the fundus.

The observation optical system 200 may have a configuration of a fundus camera type. Moreover, the OCT optical system 100 may also serve as the observation optical system 200. That is, a front image may be obtained by using two-dimensionally obtained data for generating a tomographic image. This data contains, for example, an integrated image toward a depth direction of a three-dimensional tomographic image and an integrated value of spectral data in each of X and Y positions.

<Fixation Target Projecting Unit>

The fixation target projecting unit 300 includes an optical system for guiding a direction of sight line of the eye E. The projecting unit 300 includes a fixation target to be presented to the eye E, and can guide the sight line of the eye E to a plurality of directions.

For example, the fixation target projecting unit 300 includes a visible light source for emitting a visible light, and changes a presenting position of a fixation target in a two-dimensional manner. Accordingly, a change in a direction of sight line can change a photograph portion. For example, when a fixation target is presented from the same direction as a photographing optical axis, a center portion of fundus is set as a photograph portion. Moreover, when a fixation target is presented above a photographing optical axis, an upper portion of fundus is set as a photograph portion. That is, a photograph portion is changed according to a position of a fixation target with respect to a photographing optical axis.

For example, the fixation target projecting unit 300 is configured so that a fixation position is adjusted by adjustment of a lighting state of a plurality of LEDs arranged in a matrix manner. Alternatively, the fixation target projecting unit 300 is configured so that a fixation position is adjusted by combination of scanning by an optical scanner with light of a light source and control of lighting/non-lighting of the light source. Alternatively, furthermore, the projecting unit 300 may be an internal fixation light type or an external fixation light type.

<Alignment Target>

The alignment target projecting optical system 60 projects a target light flux for alignment. In the alignment target projecting optical system 60, a plurality of infrared light sources is arranged at interval of 45 degrees on a concentric circle having a photographing optical axis L1 as a center as illustrated in a dotted area A on an upper left side of FIG. 2. The alignment target projecting optical system 60 includes a first target projecting optical system and a second target projecting optical system. The first target projecting optical system (0 degree and 180 degrees) includes two pairs of an infrared light source 61 and a collimating lens 62. Each pair is arranged symmetrically across a vertical plane that passes the photographing optical axis L1. The second target projecting optical system is arranged in a position different from that of the first target projecting optical system. The second target projecting optical system has six infrared light sources 63. The first target projecting optical system projects an infinite distance target on cornea of the eye E from a horizontal direction. The second target projecting optical system projects a finite distance target on cornea of the eye E from a vertical direction or an oblique direction. In the dotted area A illustrated in FIG. 2, a portion of the first target projecting optical system (0 degree and 180 degrees) and a portion of the second target projecting optical system (45 degrees and 135 degrees) are only illustrated for sake of simplicity.

<Anterior Segment Observation Optical System>

The anterior segment observation (photographing) optical system 80 for photographing an anterior segment of an examinee's eye includes a relay lens 84, and a two-dimensional photographing device (light receiving device) 85 having infrared region sensitivity. The relay lens 84 and the two-dimensional photographing device 85 (also referred to as a photographing device 85) are arranged on an opposite side of a dichroic mirror 24. The photographing device 85 also serves as a photographing mechanism for alignment target detection. The photographing device 85 photographs an alignment target and an anterior segment illuminated by an anterior segment illuminating light source 68 that emits an infrared light having a center wavelength of 940 nm. The light from the anterior segment illuminating light source 68 is reflected by an anterior eye segment, so that an anterior segment image is obtained. Such an anterior segment image is received by the photographing device 85 through the dichroic mirror 24 and the relay lens 84. Moreover, alignment light flux emitted from a light source included in the alignment target projecting optical system 60 is projected on the cornea of the examinee's eye. A cornea reflection image is received (projected) by the photographing device 85 through the dichroic mirror 24 and the relay lens 84. An output from the photographing device 85 is input to the control part 70. The monitor 8 displays the anterior image photographed by the photographing device 85. The anterior segment observation optical system 80 also serves as an alignment detection optical system. The alignment detection optical system includes a light receiving device (two-dimensional photographing device 85) for detecting an alignment deviation of the photographing part 3 with respect to an examinee's eye.

<Control Part>

The control part 70 controls the entire apparatus having the members 60 through 300. The control part 70 also serves as an image processing part for processing an obtained image, n image analysis part for analyzing the obtained image, and the like. The control part 70 is constructed of, for example, a general central processing unit (CPU).

The control part 70 obtains a tomographic image (OCT image) by performing an image process on a light receiving signal output from the detector 120 of the OCT optical system 100. In addition, the control part 70 obtains a front image (SLO image) based on a light receiving signal output from a light receiving device of the front observation optical system 200.

Moreover, the control part 70 detects an alignment deviation of the photographing part 3 with respect to the eye E based on a light receiving result of the photographing device 85. Thus, the control part 70 performs automatic alignment using the drive part 6 based on the detection result.

The control part 70 detects an alignment target from the anterior segment image photographed by the anterior segment observation optical system 80. The control part 70 also changes a fixation position by controlling the fixation target projecting unit 300.

The control part 70 is electrically connected with the joystick 4, the XYZ drive part 6, a memory (storage part) 72, the monitor 8, and an operation part 76. The control part 70 controls a display screen of the monitor 8. The control part 70 allows an obtained fundus image to be output on the monitor 8 as a still image or a moving image, and to be stored in the memory 72. For example, the memory 72 stores a tomographic image, a front image, and various information relating to photographing (e.g., information about photographing position, identification number, and the like of a tomographic image). The control part 70 controls the OCT optical system 100, the front observation optical system 200, and the fixation target projecting unit 300 based on operation signals output from the operation part 76. A touch panel is used as a monitor 75. Another configuration of the above OCT device 10 is described in detail in, for example, JP-A-2008-29467.

<Control Operation>

A description is now given of control operation of the present apparatus having above configuration.

Figure 3:
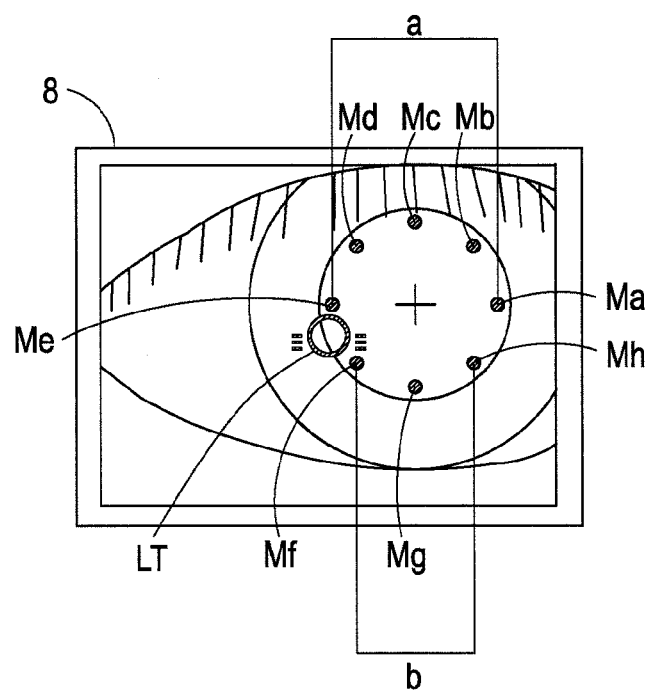
FIG. 3 is a diagram illustrating an anterior segment observation screen.

When an examiner operates the joystick 4 to move the photographing part 3, an anterior segment image is displayed on the monitor 8 with eight alignment target images Ma through Mh as illustrated in FIG. 3. Then, when the photographing device 85 detects a target image projected on a cornea Ec of the eye E, the control part 70 begins a process of automatic alignment.

<Automatic Alignment>

A description is now given of an automatic alignment process on the monitor 8. The control part 70 detects a center coordinate of XY (see a cross mark illustrated in FIG. 3) of the target images Ma through Mh projected in a ring manner. Herein, the control part 70 detects this center coordinate as a substantially corneal apex position Mo. On the photographing device 85, an alignment reference position O1 (0, 0) in XY directions is set beforehand, the alignment reference position O1 being set to have a predetermined relationship between a position of the photographing part 3 and a position of the eye E. The reference position O1 is, for example, an intersection point of a photographing surface of the photographing device 85 and a photographing optical axis L1. The alignment reference position O1 serves as an alignment reference position used for reference tomographic photographing. Moreover, an alignment acceptable range is set on the photographing device 85, the alignment acceptable range being for determination of whether or not alignment is suitable.

Figure 4:
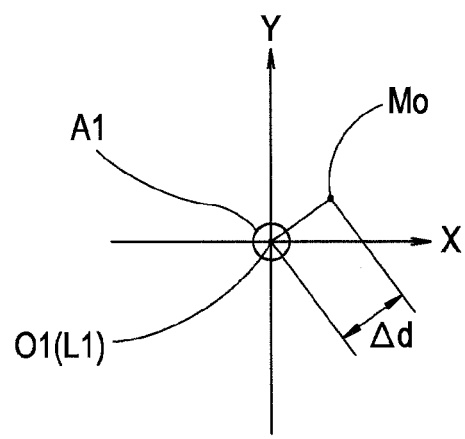
FIG. 4 is a diagram illustrating a procedure for detecting an alignment deviation.

Subsequently, the control part 70 determines a deviation amount Δd between the alignment reference position O1 and the corneal apex position Mo (see FIG. 4). The control part 70 controls driving of the XYZ drive part 6 to move the photographing part 3 such that the deviation amount Δd is provided within an acceptable range A1 (performance of the automatic alignment).

Moreover, the control part 70 compares an image ratio (a/b) between an image space "a" that is between the infinite distance target images Ma and Me, and an image space "b" that is between the finite distance target images Mh and Mf. Therefore, the control part 70 determines the alignment deviation amount Δd in a Z direction. When the photographing part 3 is deviated in a working distance direction, the image space "a" barely changes while the image space "b" changes. The control part 70 uses such characteristics to determine the alignment deviation amount in the working distance direction with respect to the eye E (see JP-A-6-46999 for detail).

In addition, the control part 70 determines a deviation amount Δd with respect to an alignment reference position in the Z direction as similar to the XY directions. The control part 70 allows the XYZ drive part 6 to perform the automatic alignment such that the deviation amount Δd is provided in the alignment acceptable range A1 of the Z direction.

When the deviation amount Δd in the XYZ directions is in the alignment acceptable range A1, the control part 70 stops the driving of the XYZ drive part 6 and outputs an alignment completion signal. Even after the completion of alignment, the control part 70 detects a deviation amount Δd as necessary. When the deviation amount Δd exceeds the acceptable range A1, the control part 70 resumes the automatic alignment. That is, the control part 70 controls (tracks) the photographing part 3 to follow the eye E such that the deviation amount Δd satisfies the acceptable range A1.

Therefore, the control part 70 controls the OCT optical system 100 to obtain a tomographic image. Moreover, the control part 70 obtains a front image by controlling the front observation optical system 200. When the alignment is performed with respect to the eye E, the control part 70 obtains a fundus tomographic image and a fundus front image. The control part 70 changes a difference in length of the optical paths for the measurement light and the reference light, so that the fundus tomographic image is obtained.

Figure 5:
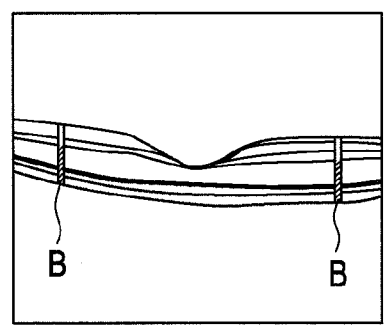
FIG. 5 is a diagram illustrating an example of a tomographic image obtained by an OCT optical system.

FIG. 5 is a diagram illustrating an exemplary tomographic image obtained by the OCT optical system 100. The tomographic image illustrated in FIG. 5 has a missing image portion B that is generated due to absorption of light by a blood vessel of a fundus. That is, a portion in shadow of a blood vessel cannot be photographed (as information cannot be obtained).

Moreover, a retinal tissue structure causes reflection intensity of measurement light at the retinal tissue to vary depending on an incident angle of the measurement light. Such variation generates a difference in depiction (how an image is captured). Consequently, a portion having low reflection intensity of the measurement light is difficult to be photographed successfully.

<Obtaining Tomographic Image at Different Incident Angles>

Now, a description is given of a process for obtaining an image of a portion that is difficult to be photographed.

The control part 70 controls the optical scanner 108 to scan a photographing region having a predetermined portion (fundus in the present embodiment) with measurement light. Thus, a photographing signal from the detector 120 is obtained. The control part 70 processes the photographing signal to obtain a tomographic image of the photographing region. The control part 70 moves the photographing part 3 to change an incident angle of the measurement light with respect to the photographing region. The control part 70, therefore, obtains a plurality of tomographic images corresponding to a plurality of different incident angles of the measurement light relating to the same photographing region. Subsequently, the control part 70 combines the plural tomographic images corresponding to the plurality of different incident angles by performing an image process to obtain a combined tomographic image. In such a case, incident angles of the measurement light to be entered into the same photographing region on the fundus are changed. When a plurality of tomographic images is obtained, photographing positions of the eye E in the respective images are preferably matched together. However, when a plurality of tomographic images is obtained, the photographing positions may be partially overlapped. As for such an overlapped portion, thus, a plurality of tomographic images for the same photographing region can be obtained.

For example, the control part 70 emits measurement light to the eye E at a first incident angle, and obtains a first tomographic image (a reference tomographic image). Subsequently, the control part 70 changes an incident angle of the measurement light. Then, the control part 70 emits the measurement light to the eye E at a second incident angle that differs from the first incident angle, and obtains a second tomographic image. Therefore, the control part 70 obtains two tomographic images that are related to the same portion of the retinal tissue, but photographed at different angles.

Subsequently, the control part 70 performs a process for combining the first tomographic image and the second tomographic image into one. For example, the control part 70 overlays the first tomographic image and the second tomographic image one on another. Alternatively, the control part 70 may obtain a mean image of the first tomographic image and the second tomographic image. The control part 70 may combine at least a portion of the first tomographic image and at least a portion of the second tomographic image by an image process. When the images are combined, a displacement may be preferably corrected by the image process in consideration of a difference in fundal inclination between the tomographic images.

An image corresponding to a missing image portion of the first tomographic image is photographed in the second tomographic image. In the combined image, thus, the missing image portion in the first tomographic image is complemented. In the combined image, that is, the photograph portion, which has been difficult to be imaged as described above, can be imaged. Therefore, a combined image having a smaller number of missing portions is generated.

Figure 6:
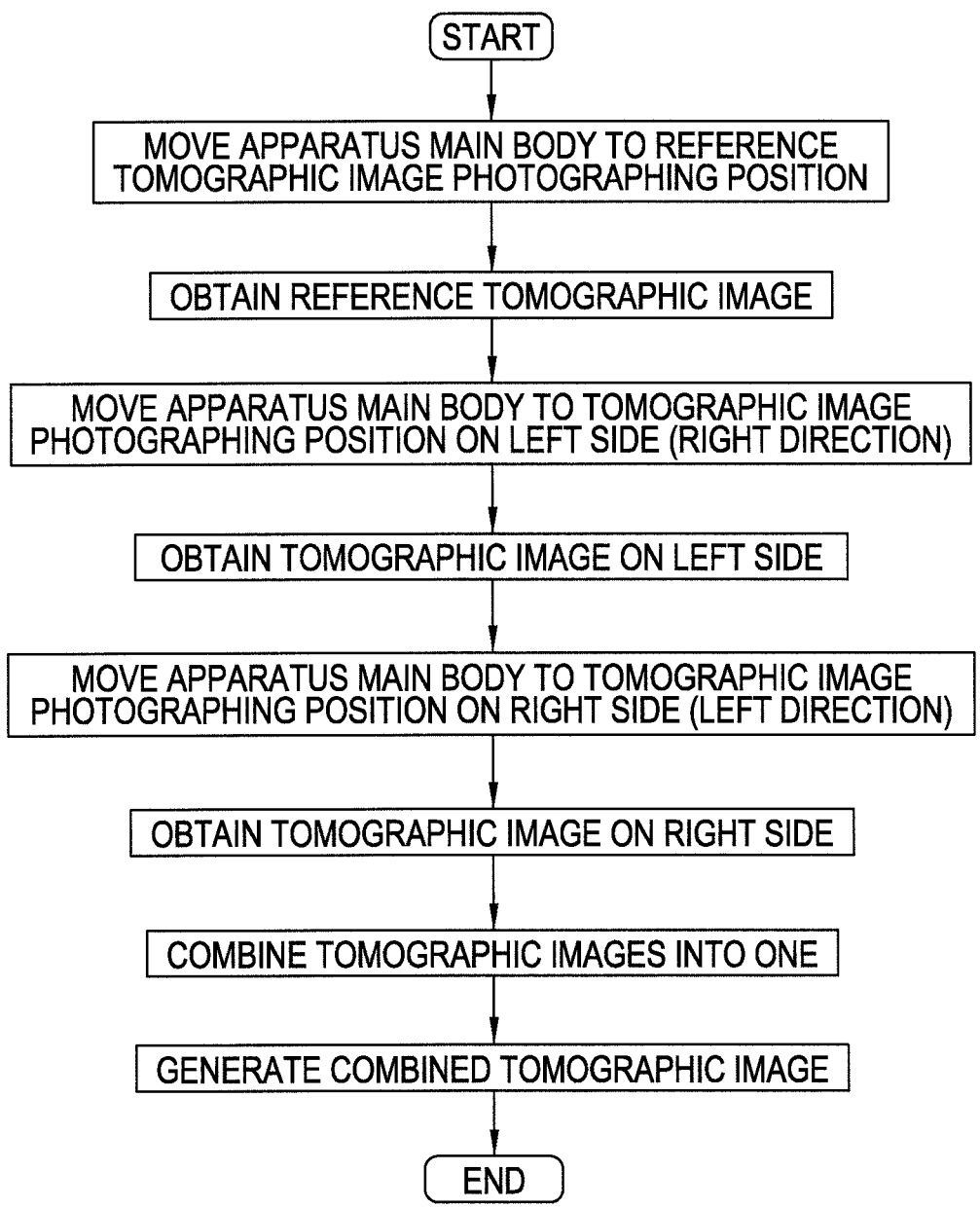
FIG. 6 is a flowchart illustrating a process for generating a combined tomographic image.

Hereinafter, the generation of a combined tomographic image is described with reference to a flowchart of FIG. 6.

In the embodiment below, the control part 70 sets incident angles to be in a front direction with respect to a photographing region and in two directions being symmetric relative to the front direction. The control part 70 obtains tomographic images with respect each incident angle for an image combining process. For example, the control part 70 changes an incident position of measurement light with respect to the cornea Ec of the eye E, thereby changing an incident angle of the measurement light with respect to the fundus Ef. For example, the control part 70 moves the photographing part 3 with respect to the eye E by driving the drive part 6. As a result, an incident position is changed.

First, the control part 70 obtains a reference tomographic image in a reference photographing position (a reference incident position). For example, a photographing position in which a photographing optical axis L1 (e.g., an optical axis of an objective lens) matches a corneal apex of an examinee is set as a reference photographing position (see FIG. 8A). An alignment reference position is set to be a reference photographing position as illustrated in FIG. 4. Under such settings, the control part 70 performs the automatic alignment with respect to the eye E. Upon completion of the alignment, the control part 70 obtains the reference tomographic image and stores the image in the memory 72 when a photographing switch 4b is operated.

Next, the control part 70 obtains second tomographic images in two second photographing positions (second incident positions) which are symmetric about the reference photographing position as a center. For example, positions deviated to the left and right from the reference photographing position are set as the second positions (see FIG. 8B and FIG. 8C). Herein, the corneal apex and the optical axis L1 are being deviated to the left or right. A photographing position capable of avoiding a vignette of measurement light in an iris is preferably set as the second photographing position.

An alignment reference position corresponding to the second position is set according to the incident angle of the measurement light with respect to the fundus. For example, the memory 72 previously stores an XY alignment reference position (FIG. 8B) to be used when a tomographic image is obtained by deviation of the photographing part 3 to the right side with respect to the eye E. Also, the memory 72 previously stores an XY alignment reference position (FIG. 8C) to be used when a tomographic image is obtained by deviation of the photographing part 3 to the left side with respect to the eye E.

Figure 7A:
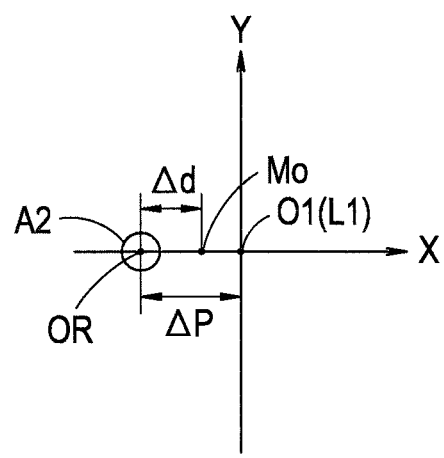
FIGS. 7A and 7B are diagrams illustrating a procedure for detecting an alignment deviation when tomographic images are respectively photographed in photographing positions that are deviated to the left side and the right side from a photographing position at the time of photographing a reference tomographic image.
Figure 7B:
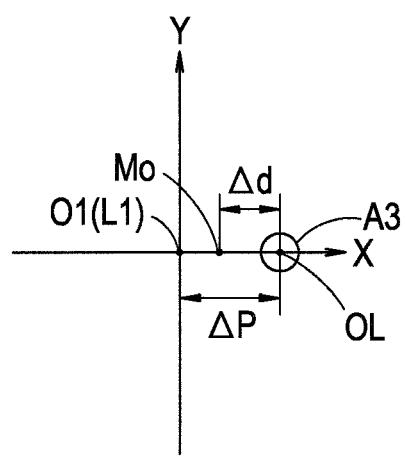

A shift amount ΔP that is from the reference photographing position to the right and left alignment reference positions corresponds to an offset amount. The control part 70 controls such that the alignment deviation amount between the alignment reference position O1 and the apex position Mo is offset by subtraction of the shift amount ΔP therefrom. Then, the control part 70 detects the alignment deviation amount Δd. In FIG. 7A, a distance from a reference position OR to a reference position O1 represents an offset amount (shift amount ΔP) that is set to photograph a tomographic image on the right side. In FIG. 7B, a distance from a reference position OL to a reference position O1 represents an offset amount that is set to photograph a tomographic image on the left side.

Herein, the control part 70 detects an alignment deviation, and then offsets the detected deviation amount by the right side or left side as described above. Then, the control part 70 performs the automatic alignment with respect to one of the eyes based on a result of the alignment detection. In this case, the control part 70 moves the photographing part 3 sequentially in two symmetric positions (a photographing position for a right tomographic image and a photographing position for a left tomographic image) with respect to the reference photographing position. Accordingly, the control part 70 obtains the second tomographic images in the respective positions. That is, the control part 70 obtains a right tomographic image and a left tomographic image for the eye E.

A second tomographic image is usually photographed after a first tomographic image is photographed. The photographing part 3 is moved to the right side and the left side symmetrically about the reference photographing position as a center with respect to the eye E (reference photographing position) at the time of photographing the second tomographic image. Therefore, two tomographic images corresponding to symmetric incident angles are obtained for the eye E.

FIGS. 7A and 7B are diagrams illustrating a procedure for detection an alignment deviation when tomographic images are photographed at photographing positions that are deviated to the left side and the right side from a photographing position at the time of photographing a reference tomographic image. When the photographing part 3 is deviated to the right side with respect to the examinee's eye (when a photographing position is set in a position to obtain a tomographic image on the left side), an alignment reference position is shifted in a direction toward the left relative to an alignment reference position used at the time of photographing a reference tomographic image (see FIG. 7A). When the photographing part 3 is deviated to the left side with respect to the eye, (when a photographing position is set in a position to obtain a tomographic image on the right side), an alignment reference position is shifted in a direction toward the right relative to an alignment reference position at the time of photographing a reference tomographic image (see FIG. 7B).

When the tomographic image on the left side (hereinafter referred to as a left tomographic image) is photographed, the photographing part 3 is moved in a direction toward the right from the reference photographing position by the automatic alignment (see FIG. 8B). When the control part 70 detects that the photographing part 3 has reached the photographing position of the left tomographic image, an alignment completion signal is output. After confirming that that an alignment target (electronic working dot) is located on a center of reticle LT, the examiner operates the photographing switch 4b. Such operation of the photographing switch 4b initiates the control part 70 to begin the photographing operation and store a photographed tomographic image in the memory 72 as a left tomographic image to be used for a combined tomographic image.

When a tomographic image on the right side (hereinafter referred to as a right tomographic image) is photographed, the photographing part 3 is moved in a direction toward the left from the reference photographing position by the automatic alignment (see FIG. 8C). When the control part 70 detects that the photographing part 3 has reached the photographing position of the left tomographic image, an alignment completion signal is output. After confirming that that the alignment target (electronic working dot) is located on a center of reticle LT, the examiner operates the photographing switch 4b. Such operation of the photographing switch 4b initiates the control part 70 to begin the photographing operation and store a photographed tomographic image in the memory 72 as a right tomographic image to be used for a combined tomographic image.

Figure 8A:
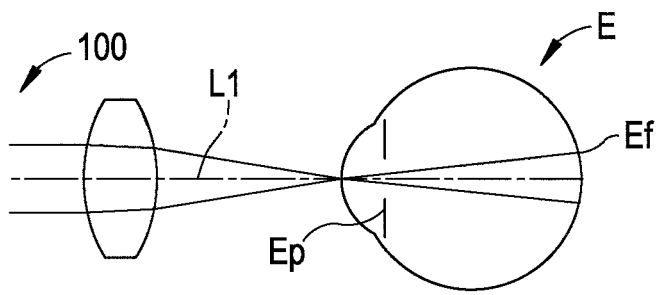
FIGS. 8A, 8B, and 8C are diagrams illustrating changes in an irradiation direction of measurement light according to changes in an incident angle with respect to the fundus of an examinee's eye.
Figure 8B:
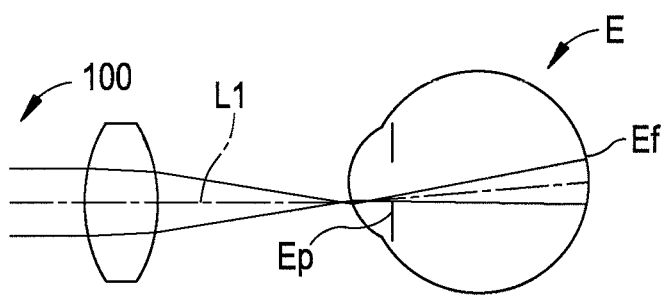
Figure 8C:
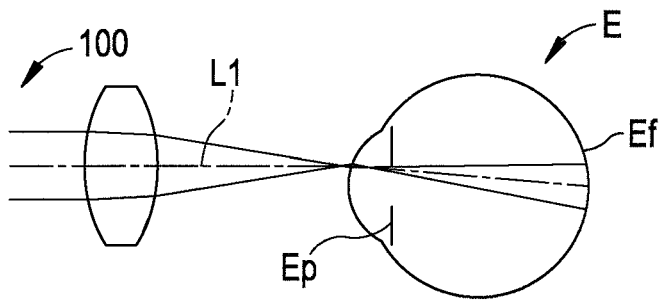
Figure 9A:
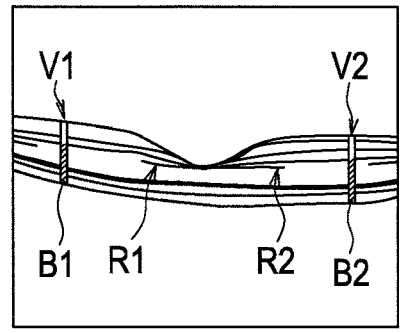
FIGS. 9A, 9B, and 9C are diagrams illustrating a plurality of tomographic images obtained when the images are photographed at different incident angles.
Figure 9B:
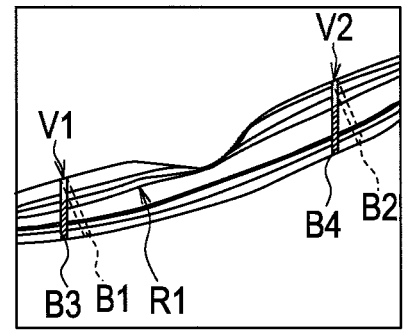
Figure 9C:
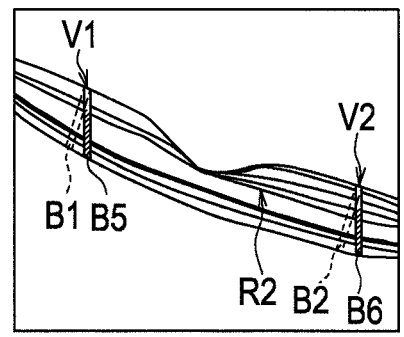

FIGS. 8A, 8B, and 8C are diagrams illustrating changes in an irradiation direction of measurement light according to changes in an incident angle with respect to the fundus, respectively. FIGS. 9A, 9B, and 9C are diagrams illustrating a plurality of tomographic images to be obtained when the images are photographed at different incident angles, respectively. FIG. 8A illustrates an irradiation state of measurement light when the photographing part 3 is arranged in a reference photographing position. FIG. 9A illustrates a tomographic image obtained when the image is photographed at the incident angle illustrated in FIG. 8A. The photographed tomographic image, for example, has missing image portions B1 and B2 that are generated due to shadows of blood vessels V1 and V2. Moreover, a retinal tissue structure causes generation of photograph portions R1 and R2 (e.g., Henle fiber layer) in which images have been difficult to be obtained.

FIG. 8B illustrates an irradiation state of measurement light when the photographing part 3 is arranged in a photographing position at the time of photographing a left tomographic image. FIG. 9B illustrates a tomographic image obtained when the image is photographed at the incident angle illustrated in FIG. 8B. In FIG. 9B, the measurement light is obliquely entered from a left direction as seen from the examinee. Thus, portions having shadows of vessels are changed from B1 (dotted line) to B3 and from B2 (dotted line) to B4. Moreover, the change in the incident angle changes a reflection angle of the measurement light at the retinal tissue, thereby generating a good image of a photograph portion R1.

FIG. 8C illustrates an irradiation state of measurement light when the photographing part 3 is in a photographing position at the time of photographing a right tomographic image. FIG. 9C illustrates a tomographic image obtained when the image is photographed at the incident angle illustrated in FIG. 8C. In FIG. 9C, the measurement light is obliquely entered from a right direction as seen from the examinee. Thus, portions having shadows of vessels are changed from B1 (dotted line) to B5 and from B2 (dotted line) to B6. Moreover, the change in the incident angle changes a reflection angle of the measurement light at retinal tissue, thereby generating a good image of a photograph portion R2.

Therefore, the missing image portions B1 and B2 and the photograph portions R1 and R2 illustrated in FIG. 9A can be photographed in the tomographic images of FIGS. 9B and 9C. An overlay of the tomographic image of FIG. 9B or 9C on the tomographic image of FIG. 9A can allow the missing image portions B1 and B2 or the photograph portions R1 and R2 to be displayed.

<Image Combining Process>

As described above, at least two tomographic images according to a plurality of different incident angles (incident positions) with respect to the fundus are obtained. Then, the control part 70 combines these tomographic images.

For example, the control part 70 detects a common feature point of each of the tomographic images. Subsequently, the control part 70 overlays a plurality of tomographic images such that the feature points of the respective tomographic images match so as to correct deviation of each of the tomographic images. In this case, the control part 70 extracts at least two feature points, and moves the tomographic image (parallel movement and rotational movement) by the image process. An example of the feature point is the blood vessel V1 positioned above the missing image portion (blood vessel shadow) B1 of FIG. 8A, the blood vessel V2 positioned above the missing image portion (blood vessel shadow) B2, or fovea centralis.

When a blood vessel or fovea centralis is to be detected from each of the tomographic images, for example, the control part 70 detects information of each layer of the fundus in the tomographic image by the image process. Then, the control part 70 analyzes the detection result of each layer based on a predetermined image determination condition (criterion), thereby detecting a blood vessel portion. The detection result with the tomographic image is stored in the memory 72 or an external memory (e.g., a memory in a personal computer or a memory in a server).

When the presence or absence of a blood vessel is to be detected, for example, the control part 70 determines the presence or absence of a shadow of the blood vessel (missing image portion). Therefore, the control part 70 determines whether there is the blood vessel in a layer (e.g., IPL) provided above the blood vessel shadow (above an A-scan direction).

When the presence or absence of the blood vessel shadow is to be determined, the control part 70 detects a luminance level of a tomographic image. Thus, a layer corresponding to a predetermined retinal layer (e.g., a retinal surface and a retinal pigment epithelial layer) is extracted by the image process. For example, the control part 70 detects a luminance distribution of an A-scan signal in each of the tomographic images. The control part 70 determines the presence or absence of the blood vessel shadow based on whether or not an increase in luminance to the retinal surface and the retinal pigment epithelial layer is detected. When the presence or absence of the blood vessel shadow is determined, for example, a layer order which has been known anatomically, a distance from the retinal surface, or strong rise in luminance with respect to a retinal surface and a retinal pigment epithelial layer may be used.

Therefore, the control part 70 can determine the presence or absence of the blood vessel shadow using each of the A-scan signals. Thus, the control part 70 obtains information regarding the presence or absence of the blood vessel in the tomographic image, thereby detecting the blood vessel on the tomographic image.

Moreover, the fovea centralis is extracted from a position within the tomographic image, a luminance distribution of the tomographic image, a shape distribution of the tomographic image, and the like. The fovea centralis has low luminance for periphery thereof, and has a shape of circle. The control part 70 performs the image process to extract an image region that matches these features.

When the detection of the feature point is finished, the control part 70 corrects a position deviation by performing an image process (e.g., affine transformation process or a scale changing process). Herein, the control part 70 corrects an inclination difference of photograph portion in each of the tomographic images by the image process.

For example, the control part 70 moves a left tomographic image (see FIG. 9B) and a right tomographic image (see FIG. 9C) using a reference tomographic image as a reference, so that a position deviation is corrected. Herein, the inclinations of the right tomographic image and the left tomographic image are preferably corrected such that photograph portions in the right and left tomographic images substantially match photograph portions in the reference tomographic image.

Figure 10:
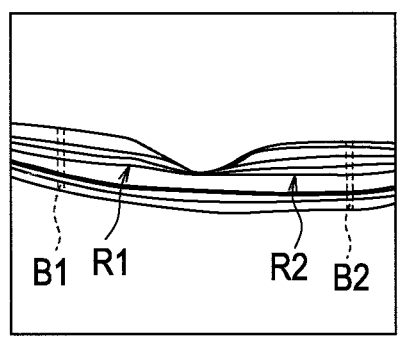
FIG. 10 is a diagram illustrating a combined tomographic image.

After the correction, the control part 70 obtains a mean image relating to three tomographic images, and generates a combined tomographic image (see FIG. 10). The control part 70 stores the combined tomographic image in the memory 72. The control part 70 allows the combined tomographic image stored in the memory 72 to be displayed on the monitor 8 or printed by a printer.

According to the image combing process, therefore, the missing image portions in the tomographic image are complemented. Thus, a good tomographic image can be obtained. Moreover, the photographing is performed a plurality of times at different incident angles, thereby readily capturing an image of a fibrous layer of the retinal cell which has had difficulty in being imaged.

Therefore, a portion which has not been analyzed precisely due to a blood vessel can be analyzed. Thus, more precise information on such a portion can be obtained.

In the above description, a movement of the photographing part 3 (apparatus main body) changes an incident angle. However, a change in the incident angle is not limited thereby. A member for changing an incident angle of measurement light with respect to a photographing region may be used. For example, an optical member that is insertable into or detachable from an optical system may be arranged (e.g., prism). In such a case, an incident angle of measurement light can be changed by insertion or detachment of the prism. Alternatively, a rotary prism capable of rotating around the optical axis L1 may be used. In such a case, the number of prisms to be used can be reduced.

In the above description, a reference tomographic image, and right and left tomographic images with the reference tomographic image as a center thereof are obtained and then combined. Alternatively, at least one tomographic image may be obtained at an incident angle that differs from that used to obtain a reference tomographic image, and the tomographic image and the reference tomographic image may be combined. Even in this case, a missing image portion of the reference tomographic image can be complemented.

A photographing position of the second tomographic image is a different from a reference photographing position such that an incident angle of measurement light at a fundus differs from that used by the reference photographing position. For example, two or more tomographic images corresponding to different incident angles in a vertical direction may be obtained and combined. In addition, tomographic images corresponding to two or more photographing positions in directions deviated from a reference photographing position may be obtained and combined (e.g., a left tomographic image and an upper tomographic image). The reference tomographic image and the left tomographic image as described above may be combined. That is, a pair of tomographic images with respect to a reference tomographic image may not be necessarily obtained.

The number of tomographic images to be obtained for a combining process may be set according to the needs of an examiner. The present apparatus may have a configuration in which the examiner can optionally set the number of tomographic images to be obtained. In addition, the present apparatus may have a plurality of photographing modes according to observation needs. The predetermined number of tomographic images to be obtained may be set beforehand according the photographing mode.

In the above description, the automatic alignment is performed. Thus, a plurality of tomographic images corresponding to a plurality of different incident angles is smoothly photographed. However, such automatic alignment may not be performed. For example, an examiner may obtain by tomographic images at optional photographing positions by operating the joystick 4. Then, the control part 70 combines the tomographic images having different incident angels as described above.

In the above description, a photographing position is set by automatic alignment, but is not limited thereby. The present apparatus may have a guide mechanism for setting an incident angle to be a predetermined angle position. For example, the guide mechanism may be configured to allow a guide to be displayed on the monitor 75 based on an alignment detection result. Moreover, when the above-described prism is arranged to change an incident angle, for example, the prism may be automatically rotated to a predetermined angle. In addition, a guide may be displayed to guide a rotary prism to a predetermined angle.

In the above description, detection of a corneal raster detects an alignment state with respect to the eye E. Alternatively, an alignment state may be detected by detection of a feature portion of the eye E by an image process. For example, an alignment state may be detected by detection of a pupil center of the eye E. In this case, a position in which the pupil center and the optical axis L1 are matched may be used as the reference photographing position as described above.

A change in an incident angle of measurement light with respect to a fundus may cause a deviation of a scanning direction of the measurement light on the fundus (tomographic photographing position). Thus, a scanning position of the measurement light may be preferably adjusted according to a change in the incident angle. In such a case, an examiner may correct the scanning position on the fundus. Alternatively, a correction amount may be determined beforehand, and a scanning position on the fundus may be corrected according to a change in the incident angle.

The embodiment has been applied to a fundus photographing apparatus in the above disclosure, but is not limited thereto. The disclosed embodiment may be applied to, for example, an anterior segment photographing apparatus.

When an anterior segment tomographic image is analyzed, an incident angle of measurement light prior to incident on a cornea is changed. That is, for example, a fixation target projecting unit for guiding the sight line of the eye E is used to change an incident angle of measurement light with respect to a certain photographing region of an anterior eye segment. In this case, the incident angle of the measurement light is changed according to a change in a direction of the sight line. Alternatively, the photographing part 3 may make a tilt movement about an examinee's eye as a rotation axis to change an incident angle.

When an incident angle is changed, an optical path length for measurement light or reference light may be adjusted again. A position of a tomographic image of the eye E in the Z direction may be adjusted by such an optical path length adjustment. Moreover, when position deviations of a reference tomographic image, a left tomographic image, and a right tomographic image are corrected, an inclination of a photograph portion in each image may be corrected such that the photograph portion in each tomographic image is perpendicular to a depth direction.

The ophthalmic photographing apparatus according to the disclosed embodiment can be provided as first through eighth ophthalmic photographing apparatuses below. That is, the first ophthalmic photographing apparatus includes: an interference optical system having a light source, a splitter configured to split a light emitted from the light source to a measurement optical path in which an examinee's eye is arranged and a reference optical path, and an optical detector configured to receive combined light of a light from the measurement optical path by being reflected by the examinee's eye and a light from the reference optical path; an optical scanner configured to be arranged in the measurement optical path and to scan a photographing region on the examinee's eye with light; a controller configured to obtain a tomographic image in the photographing region by controlling the optical scanner and processing an output signal from the optical detector; and an image processor configured to obtain a combined tomographic image by combining a plurality of tomographic images having different incident angles by an image process.

The second ophthalmic photographing apparatus is provided according to the first ophthalmic photographing apparatus, and the image processor corrects inclination of photograph portions in each of the plurality of tomographic images having different incident angles by the image process.

The third ophthalmic photographing apparatus is provided according to the first ophthalmic photographing apparatus, and further includes an incident angle changing unit configured to change an incident angle of the light with respect to each scanning position on the photographing region.

The fourth ophthalmic photographing apparatus is provided according to the third ophthalmic photographing apparatus. The forth ophthalmic photographing apparatus photographs a fundus of the eye of an examinee, and the incident angle changing unit changes the incident angle of the light with respect to the fundus by changing an incident position of the light with respect to a cornea of the eye.

The fifth ophthalmic photographing apparatus is provided according to the third ophthalmic photographing apparatus, and the incident angle changing unit includes a guide unit configured to set the incident angle to be a predetermined angle position.

The sixth ophthalmic photographing apparatus is provided according to the first ophthalmic photographing apparatus, and each of the plurality of tomographic images having different incident angles is an image in substantially the same photographing region.

The seventh ophthalmic photographing apparatus is provided according to the third ophthalmic photographing apparatus, and the incident angle changing unit is at least any of a drive part configured to move an apparatus main body which stores therein the interference optical system and the optical scanner, or an optical member configured to change an incident angle of measurement light.

The eighth ophthalmic photographing apparatus includes an image obtaining part configured to obtain a plurality of tomographic images corresponding to a plurality of different incident angles, and an image combining part configured to obtain a combined tomographic image by combining the plurality of tomographic images.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmic photographing apparatus, comprising:
an interference optical system having
a light source,
a splitter configured to split light emitted from the light source into measurement light traveling toward an examinee's eye and reference light, and
an optical detector configured to receive combined light of the measurement light reflected by the examinee's eye and the reference light;
an optical scanner configured to be arranged in an optical path of the measurement light and to scan a photographing region of the examinee's eye with the measurement light;

a controller configured to obtain a tomographic image of the photographing region by controlling the optical scanner and processing an output signal from the optical detector; and an image processor configured to
obtain a combined tomographic image by combining a plurality of tomographic images corresponding to a plurality of different incident angles, and
correct a difference in inclination of photograph portions among the plurality of tomographic images corresponding to the plurality of different incident angles.

2. The ophthalmic photographing apparatus according to claim 1, further comprising:
an incident angle changing unit configured to change an incident angle of the measurement light with respect to the photographing region.

3. The ophthalmic photographing apparatus according to claim 2, wherein
the apparatus is configured to photograph a fundus of the examinee's eye, and
the incident angle changing unit is configured to change the incident angle of the measurement light with respect to the fundus by changing an incident position of the measurement light with respect to a cornea of the eye.

4. The ophthalmic photographing apparatus according to claim 2, wherein
the incident angle changing unit includes a guide unit configured to set the incident angle of the measurement light to a predetermined angle.

5. The ophthalmic photographing apparatus according to claim 1, wherein
the plurality of tomographic images corresponding to the plurality of different incident angles includes images relating to substantially the same photographing region.

6. The ophthalmic photographing apparatus according to claim 2, further comprising:
an apparatus main body configured to house the interference optical system and the optical scanner,
wherein
the incident angle changing unit is a drive part configured to move the apparatus main body.

7. The ophthalmic photographing apparatus according to claim 2, wherein
the incident angle changing unit is an optical member configured to change the incident angle of the measurement light.

8. An ophthalmic photographing apparatus, comprising:
an interference optical system having
a light source,
a splitter configured to split light emitted from the light source into measurement light traveling toward an examinee's eye and reference light, and
an optical detector configured to receive combined light of the measurement light reflected by the examinee's eye and the reference light;
an optical scanner configured to be arranged in an optical path of the measurement light and to scan a photographing region of the examinee's eye with the measurement light;
a controller configured to obtain a tomographic image of the photographing region by controlling the optical scanner and processing an output signal from the optical detector;
an incident angle changing unit configured to change an incident angle of the measurement light with respect to the photographing region; and
an apparatus main body configured to house the interference optical system and the optical scanner,
wherein
the incident angle changing unit is a drive part configured to move the apparatus main body.

9. The ophthalmic photographing apparatus according to claim 8, wherein the controller is configured to
based on an image of an anterior segment of the examinee's eye, detect an alignment deviation of the ophthalmic photographing apparatus with respect to the examinee's eye, and
based on the detected alignment deviation and by controlling the drive part, cause the ophthalmic photographing apparatus to follow the examinee's eye to obtain a tomographic image of the photographing region at a set incident angle.

10. The ophthalmic photographing apparatus according to claim 9, wherein
the set incident angle is such that the measurement light obliquely enters the examinee's eye.

* * * * *